US 8,439,933 B2

(12) United States Patent
Akahoshi

(10) Patent No.: US 8,439,933 B2
(45) Date of Patent: May 14, 2013

(54) DOUBLE LUMEN PHACOEMULSIFICATION NEEDLE TIP

(75) Inventor: Takayuki Akahoshi, Tokyo (JP)

(73) Assignee: Art, Limited, Grand Cayman (KY)

( * ) Notice: Subject to any disclaimer, the term of this patent is extended or adjusted under 35 U.S.C. 154(b) by 113 days.

(21) Appl. No.: 12/399,980

(22) Filed: Mar. 8, 2009

(65) Prior Publication Data

US 2009/0227937 A1 Sep. 10, 2009

Related U.S. Application Data

(60) Provisional application No. 61/035,024, filed on Mar. 9, 2008.

(51) Int. Cl.
*A61F 9/00* (2006.01)
(52) U.S. Cl.
USPC .......................................... 606/107; 606/169
(58) Field of Classification Search ...... 604/22; 606/107, 606/161, 162, 169, 170, 171; 623/6.12
See application file for complete search history.

(56) References Cited

U.S. PATENT DOCUMENTS

| | | | | |
|---|---|---|---|---|
| 4,061,146 A | * | 12/1977 | Baehr et al. | 606/107 |
| 4,493,694 A | * | 1/1985 | Wuchinich | 604/22 |
| 4,921,476 A | * | 5/1990 | Wuchinich | 604/22 |
| 5,653,724 A | * | 8/1997 | Imonti | 606/169 |
| 6,579,270 B2 | * | 6/2003 | Sussman et al. | 604/275 |
| 2002/0077585 A1 | * | 6/2002 | Sussman et al. | 604/22 |
| 2002/0099325 A1 | * | 7/2002 | Sutton et al. | 604/22 |
| 2004/0267211 A1 | * | 12/2004 | Akahoshi | 604/264 |
| 2006/0052758 A1 | * | 3/2006 | Dewey | 604/272 |
| 2006/0100653 A1 | * | 5/2006 | Akahoshi | 606/169 |
| 2006/0135976 A1 | * | 6/2006 | Perkins | 606/171 |

OTHER PUBLICATIONS http://www.thefreedictionary.com/bell, retrieved on Mar. 25, 2012.*
http://www.thefreedictionary.com/rigid, retrieved Mar. 25, 2012.*

* cited by examiner

*Primary Examiner* — Ryan Severson
*Assistant Examiner* — David Eastwood
(74) *Attorney, Agent, or Firm* — Jerry A. Schulman

(57) ABSTRACT

A phacoemulsifcation needle has a central aspiration passageway extending through a needle body. A hollow shell is attached to and covers at least a portion of the needle body, creating an annular space between the inner surface of the shell and the outer surface of the needle body. At least one port is formed through the needle body communicating between the aspiration passageway and the annular space to create a flow path. The openings to the needle body and the shell may be coplanar or may lie in different planes.

6 Claims, 3 Drawing Sheets

DOUBLE LUMEN PHACOEMULSIFICATION NEEDLE TIP

This application claims priority from U.S. Patent Application Ser. No. 61/035,024, filed 9 Mar. 2008 and entitled "Double Lumen Phacoemulsification Needle Tip", which is incorporated herein in its entirety by reference.

FIELD OF THE INVENTION

This disclosure relates to surgical instruments and surgical techniques used in eye surgery and more particularly, to phacoemulsification apparatus and methods for their use.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such removal technique is known as phacoemulsification. A typical phacoemulsification tool includes a handpiece to which is attached a hollow needle. Electrical energy is applied to vibrate the needle at ultrasonic frequencies in order to fragment the diseased lens into small enough particles to be aspirated from the eye through the hollow needle. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse.

Phacoemulsification needles and tips are well represented in the prior art. Needles and tips of varying configurations are well known. A particular shape for a tip or needle is often dictated by the type of handpiece with which the needle is to be used.

United States Patent Application Publication 2006/0217672 (Chon) teaches and describes a phacoemulsification tip that is swaged or crimped at its distal end. The tip is intended for use with a handpiece producing torsional motion and the crimping forms cutting edges at the distal end.

U.S. Pat. No. 5,725,495 (Strukel et al) teaches and describes a phacoemulsification handpiece, sleeve and tip illustrating a wide variety of tip configurations and needle cross-sectional configurations.

U.S. Pat. No. 6,007,555 (Devine) teaches and describes an ultrasonic needle for surgical emulsification. The needle and its tip are shown in both circular and oval configurations.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

U.S. Pat. No. 5,645,530 (Boukhny) teaches and describes a phacoemulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

Published U.S. Patent Application No. 2003/0004455 (Kadziauskas) teaches and describes a bi-manual phaco needle using separate emulsification and aspiration needles inserted into the eye simultaneously during surgery.

U.S. Pat. No. 6,077,285 (Boukhny) teaches and describes a torsional ultrasound handpiece configured to impart both longitudinal and torsional motion to a phacoemulsification needle.

U.S. Pat. No. 6,402,769 (Boukhny) is a continuation in part of the '285 patent and further particularizes the frequencies at which the crystals providing both the torsional and longitudinal motion are activated.

I have determined that improved results can be achieved if the phacoemulsification tip is provided with more than one aspiration lumen. I have also determined that these improved results can be achieved using the straight phacoemulsification needle configuration, a configuration which is favored by a considerable number of doctors.

In addition, the tip design is expected to enhance the emulsifying defect created by a phacoemulsification handpiece imparting torsional motion to a phacoemulsifcation needle. Improved results are also anticipated when the present invention is used with a phacoemulsifcation handpiece providing longitudinal motion.

In accordance with an example of the apparatus, a phacoemulsification needle is provided for use with a phacoemulsification handpiece with the needle having at least two aspiration lumens formed proximate the needle tip opening. Preferably, both lumens communicate with a central aspiration passageway formed in the needle body.

While the following describes an example or examples of the present invention, it is to be understood that such description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures

BRIEF DESCRIPTION OF THE DRAWINGS

These and further aspects of the present invention will be best understood by reference to the accompanying drawings wherein.

DETAILED DESCRIPTION OF THE INVENTION

Figure 1:
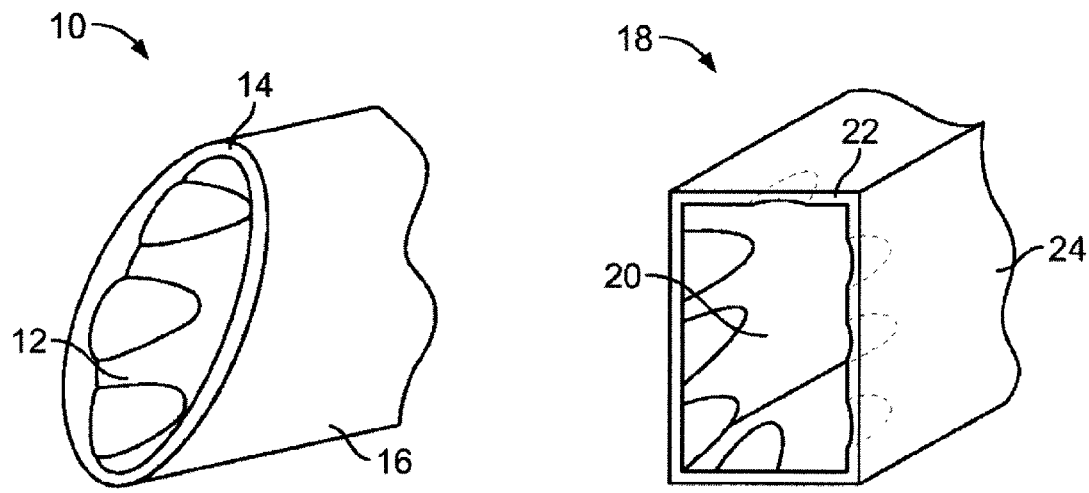
FIG. 1 is a drawing showing prior art oval and square-shaped tips.

Referring now to FIG. 1, the numeral 10 indicates generally a prior art phacoemulsification needle tip as shown in U.S. Pat. No. 6,007,555. Needle 10 terminates in a mouth 12 defined by a lip 14 at the end of needle body 16, with lip 14 and needle body 16 formed as having an oval cross-section configuration.

Referring to FIG. 1, the numeral 18 indicates generally a prior art phacoemulsification needle tip from U.S. Pat. No. 6,007,555, having a mouth 20 defined by a lip 22 at the end of needle 24. The cross-sectional configuration of needle 18 and mouth 20 is a rectangle.

Figure 2:
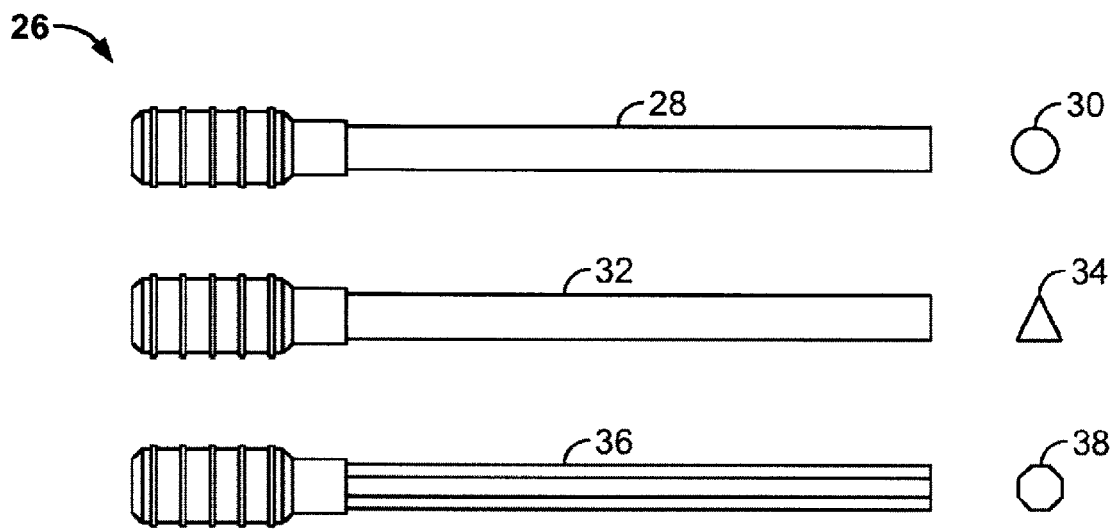
FIG. 2 is a drawing showing several prior art needle cross-sectional configurations.

Referring now to FIG. 2, the numeral 26 identifies several prior art phacoemulsification needles as described in U.S. Pat. No. 5,725,495, with needle 28 having a circular cross-section as shown at 30, needle 32 having a triangular cross-section as shown at 34 and needle 36 having an octagonal cross-section as shown at 38.

Figure 3:
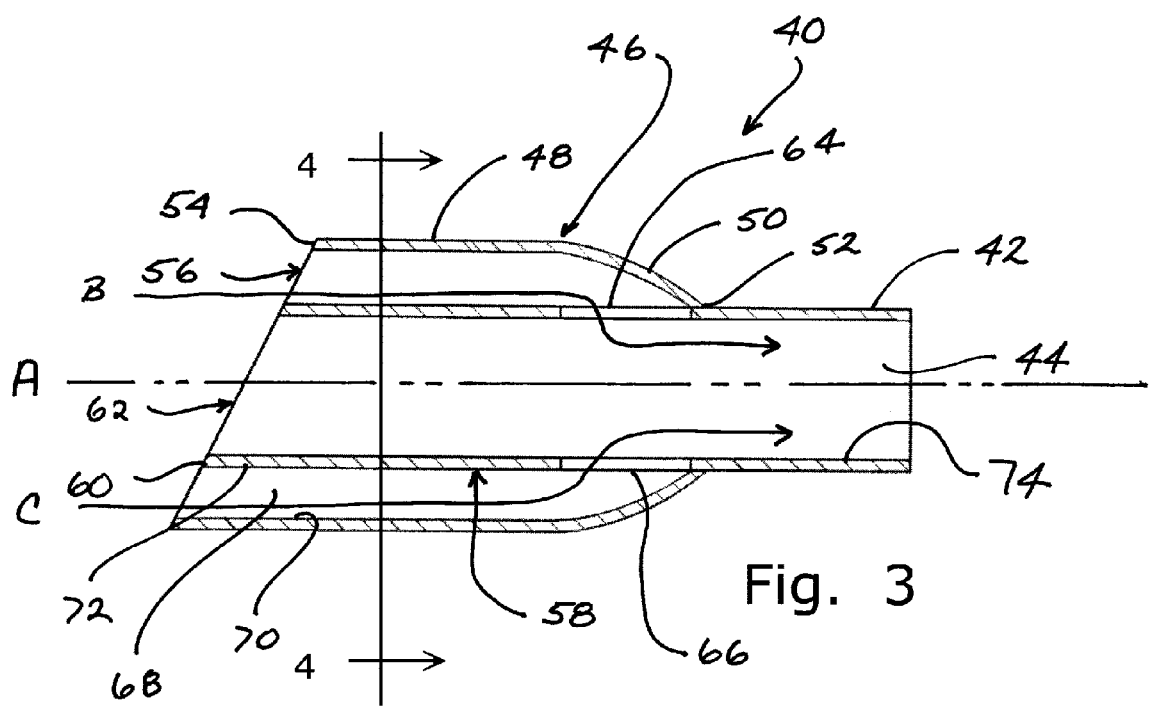
FIG. 3 is a lateral sectional view of a phacoemulsification needle tip embodying aspects of the present invention.

Referring now to FIG. 3, the numeral 40 identifies a phacoemulsification needle embodying certain aspects of the present invention. Needle 40 has a straight hollow body 42 within which a central aspiration passageway 44 is formed. Passageway 44 forms a lumen, that is, a structure described as a bore of a tube, such as a hollow needle. In the embodiment shown, needle 40 has an outer, bell-shaped shell 46 having a first, substantially straight wall portion 48 and a second, curved wall portion 50 curving down to be joined liquid-tightly to body 42 at a juncture 52. The term "juncture" is used here to identify that place at which shell 46 is attached to body 42.

In this described embodiment, shell 46 has a circular cross-section as does passageway 44. It is also contemplated that the principles of the present invention will apply to tips that are angled with respect to body 42 or to tips that are mounted to an angled portion of body 42. It is also expected that the principles of the present invention will apply to different cross-sectional configurations of shell 46 and different cross-sectional configurations of body 42.

Figure 4:
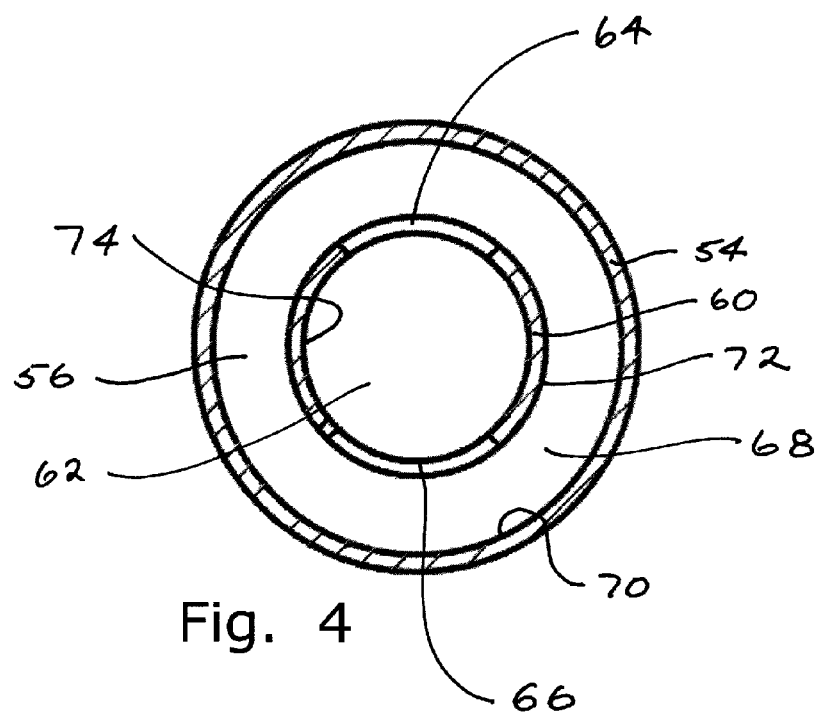
FIG. 4 is a view along line 4-4 of Fig.

Shell 46 terminates at a lip 54, which, as seen in FIG. 4, defines a shell mouth 56. In the example shown in FIG. 3, shell mouth 56 is formed at an angle to a central axis A of needle body 42. It is contemplated that the principles of the present invention may be applied at various other angles of inclination for shell mouth 56 including having shell mouth 56 formed perpendicularly to axis A.

There are known phacoemulsifcation needles that have flared tips similar in shape as shell 46. In such needles, body 42 would thus terminate at juncture 52. It is a feature of the present invention that a distal portion 58 of body 42 extends into shell 46 and, in the embodiment shown, terminates at a body lip 60 which defines a body mouth 62.

Shell 46 and body 42 are used, inter alia, to aspirate emulsified tissue particles from the eye during phacoemulsification surgery through aspiration passageway 44 which defines a flowpath for aspirated particles and liquid.

Referring again to FIG. 3, a first body port 64 and a second body port 66 are shown as formed through distal body portion 58. In the example shown, ports 64, 66 are formed within shell 46 intermediate lip 60 and the point where curved wall portion 50 joins body 44. It is to be understood that the number, shape, size and position of such ports may be varied as desired.

As seen in FIGS. 3 and 4 an annular flow space 68 is defined by the inner wall 70 of shell 46 and the outer wall 72 of distal portion 58. Annular space 68 communicates with passageway 44 via ports 64, 66 and function to create an aspiration path through tip mouth 50 to as illustrated at B and C in FIG. 3.

FIG. 4 shows that ports 64, 66 are located diametrically opposite one another. It should be understood that a varying number of ports can be used and that such ports can be staggered with respect to each other rather than being formed directly opposite one another. While not herein specifically shown, ports 64, 66 are circular, but may also be formed as ovals or other shapes as well.

It is to be understood that in describing the principles of the present invention, shell mouth 56 is defined as the opening to the annular space 68 formed between the inner wall 70 of shell 46 and the outer wall 72 of body 42. Needle body mouth 62 is defined as the opening to passageway 44 which, in turn, is defined by inner body wall 74.

As shown in its present configuration, tip 40 thus provides a first cutting or emulsifying surface defined by lip 54 and a second cutting or emulsifying surface defined by lip 60. In addition, should shaft mouth 62 become occluded, fluid flow and particle aspiration can be maintained through tip mouth 50. Where tip mouth 50 is occluded, shaft mouth 62 is likewise available for aspiration.

Figure 5:
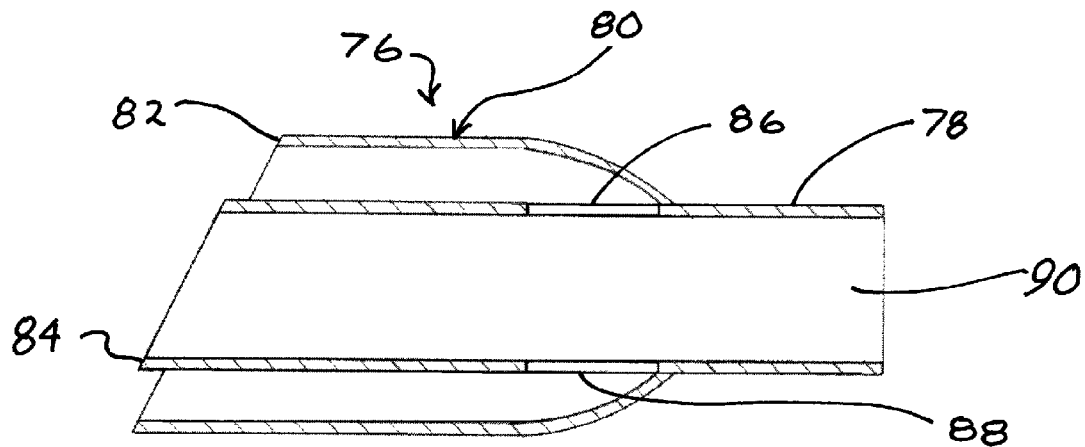
FIG. 5 is a lateral sectional view of a second embodiment of the present invention.

While lips 54 and 60 are shown in this embodiment as lying in a single plane, it is contemplated that variations on this configuration where said lips lie in different planes will also be effective. Referring now to FIG. 5 a needle 76 is shown having a needle body 78 to which a shell 80 has been joined. Shell 80 is flared out and surrounds needle body 78 as described above in connection with FIGS. 3 and 4. Shell 80 terminates at a lip 82 while needle body 78 terminates a lip 84. As shown in FIG. 5, lip 82 is not coplanar with lip 84 and, in the example shown, lip 84 extends past lip 82. Other configurations of lips 82, 84 are also possible as, for example, with lip 82 extending past lip 84. As described above, ports 86, 88 are formed within shell 80.

Figure 6:
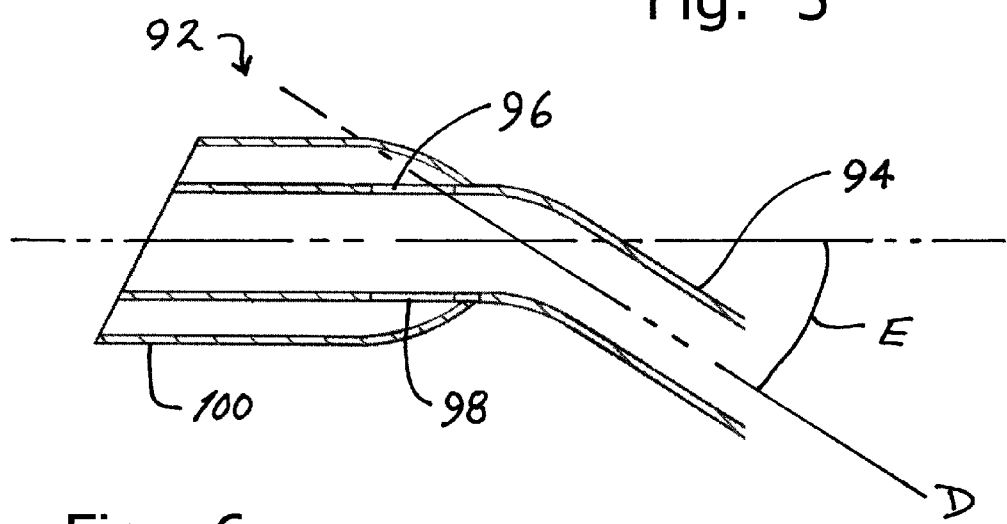
FIG. 6 is a lateral sectional view of a third embodiment of the present invention.

The examples of FIGS. 3, 4 and 5 are drawn to a shaft-and-tip configuration wherein the tip and the shaft are coaxial, that is, centered on axis A. In FIG. 6 a tip 92 having needle body 94 is shown constructed in accordance with the foregoing descriptions, with ports 96, 98 formed within shell 100. In this embodiment, however, needle body 94 is formed at an angle to shell 100, measured as an angle E to needle body axis D.

Figure 7:
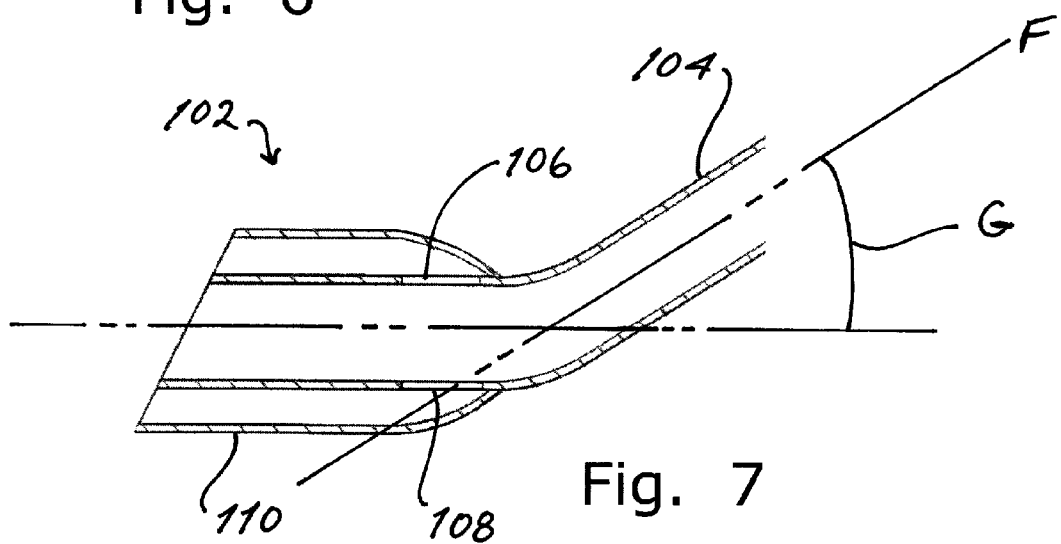
FIG. 7 is a lateral sectional view of a fourth embodiment of the present invention.

Similarly, in FIG. 7, a tip 102 having needle body 104 is shown constructed in accordance with the foregoing descriptions, with ports 106, 108 formed within shell 110. In this embodiment, however, needle body 104 is formed at an angle to shell 110, measured as an angle G to needle body axis F.

I claim:

1. A phacoemulsification needle for aspirating liquid and tissue particles from a surgical site, said needle comprising:
a needle body having a distal end and a proximal end,
said needle body having a central bore,
said bore having a central axis, said needle body terminating at a needle body lip,
said needle body lip defining a needle body mouth communicating with said bore;
a bell-shaped hollow shell having first and second ends,
said second end attached fluid-tightly to said needle body at a juncture,
said shell flaring outward from said needle body from said second end toward said first end,
said first end terminating at a shell lip,
said shell lip defining a shell mouth,
said shell and said needle body defining therebetween an annular flow space for aspirating liquid from said surgical site;
at least one port formed through said needle body intermediate said needle body lip and said juncture, whereby said annular space communicates with said bore by way of said at least one port,
said bore, said annular flow space, said shell mouth and said needle body mouth defining a flow path for aspirating liquid and tissue particles from said surgical site,
said shell lip and said needle body lip defining first and second cutting surfaces configured to emulsify tissue.

2. The apparatus as recited in claim 1 wherein said needle body lip and said shell lip are substantially coplanar.

3. The apparatus as recited in claim 1 wherein said needle body lip and said shell lip lie in different planes.

4. The apparatus as recited in claim 1 wherein said needle body lip extends past said shell lip.

5. The apparatus as recited in claim 1 wherein said needle has two said ports.

6. The apparatus as recited in claim 1 wherein said shell has a central shell axis, said shell axis being angled with respect to said needle body axis.

* * * * *